United States Patent
Li et al.

(10) Patent No.: US 12,344,593 B2
(45) Date of Patent: Jul. 1, 2025

(54) METHOD MELT CRYSTALLIZATION FOR PREPARING HIGH-PURITY GLABRIDIN

(71) Applicants: Guangzhou Fanzhirong Cosmetics Co., LTD., Guangzhou (CN); Guangzhou Qingnang Biotechnology Co., LTD., Guangzhou (CN)

(72) Inventors: Anzhang Li, Guangzhou (CN); Anning Wang, Guangzhou (CN); Lushi Cheng, Guangzhou (CN)

( * ) Notice: Subject to any disclaimer, the term of this patent is extended or adjusted under 35 U.S.C. 154(b) by 0 days.

(21) Appl. No.: 18/657,828

(22) Filed: May 8, 2024

(65) Prior Publication Data

US 2025/0066317 A1    Feb. 27, 2025

(30) Foreign Application Priority Data

Aug. 22, 2023  (CN) .......................... 202311064877.2

(51) Int. Cl.
*C07D 311/78*    (2006.01)
(52) U.S. Cl.
CPC .................................. *C07D 311/78* (2013.01)
(58) Field of Classification Search
CPC .................................................. C07D 311/78
See application file for complete search history.

(56) References Cited

FOREIGN PATENT DOCUMENTS

| CN | 101735233 | * | 6/2010 |
|---|---|---|---|
| CN | 101735233 | A | 6/2010 |
| CN | 104725394 | A | 6/2015 |
| CN | 110922413 | * | 3/2020 |

OTHER PUBLICATIONS

Jing, Yi; Jing, Rong-Qin; Ren, Yuan; Hu, Tian-hui; Study on the separation and purification of the total flavonoids in the Stigma maydis by AB-8 macroporous absorption resins; Zhongyiyao Xuebao (2010), 38(1), 75-78.*
People's Republic of China Light Industry Standard, Cosmetic Ingredients-Glycyrrhiza Glabra (Licorice) Root Extract, published on Apr. 5, 2016.
He Zhi-wen, Shen Ye-xiang, Liu Wei-hua, et al., Study on Synthesis and Pharmacological Activities of Glabridin, published on Jan. 2023.
Wang Xu-dong, Wang Zi-wei, Sun Chao-hui, Chai Bao-shan, Progress on the Synthesis of Glabridin, published on Jun. 2021.
CN202311064877.2, 1st Office Action, dated Dec. 19, 2023.
CN202311064877.2, Notice of Allowance, dated Jan. 3, 2024.

* cited by examiner

*Primary Examiner* — Valerie Rodriguez-Garcia

(57) ABSTRACT

The present invention provides a melt crystallization method for preparing high-purity glabridin, belonging to the field of chemical purification technology. The method mainly includes steps of melt crystallization, sweating, and material melting. This invention adopts a fractionating melt crystallization method to purify glabridin. The melt crystallization method was utilized in the present invention for purification, and can obtain ultra-high purity products with purity more than 99.9%. This method has the characteristics of simple operation, no need for a large amount of solvent, high product purity, environmental protection, and low energy consumption. It is a green separation and purification process. The technology is suitable for high demand of the market on high-purity glabridin, and has strong market competitive advantages.

9 Claims, 1 Drawing Sheet

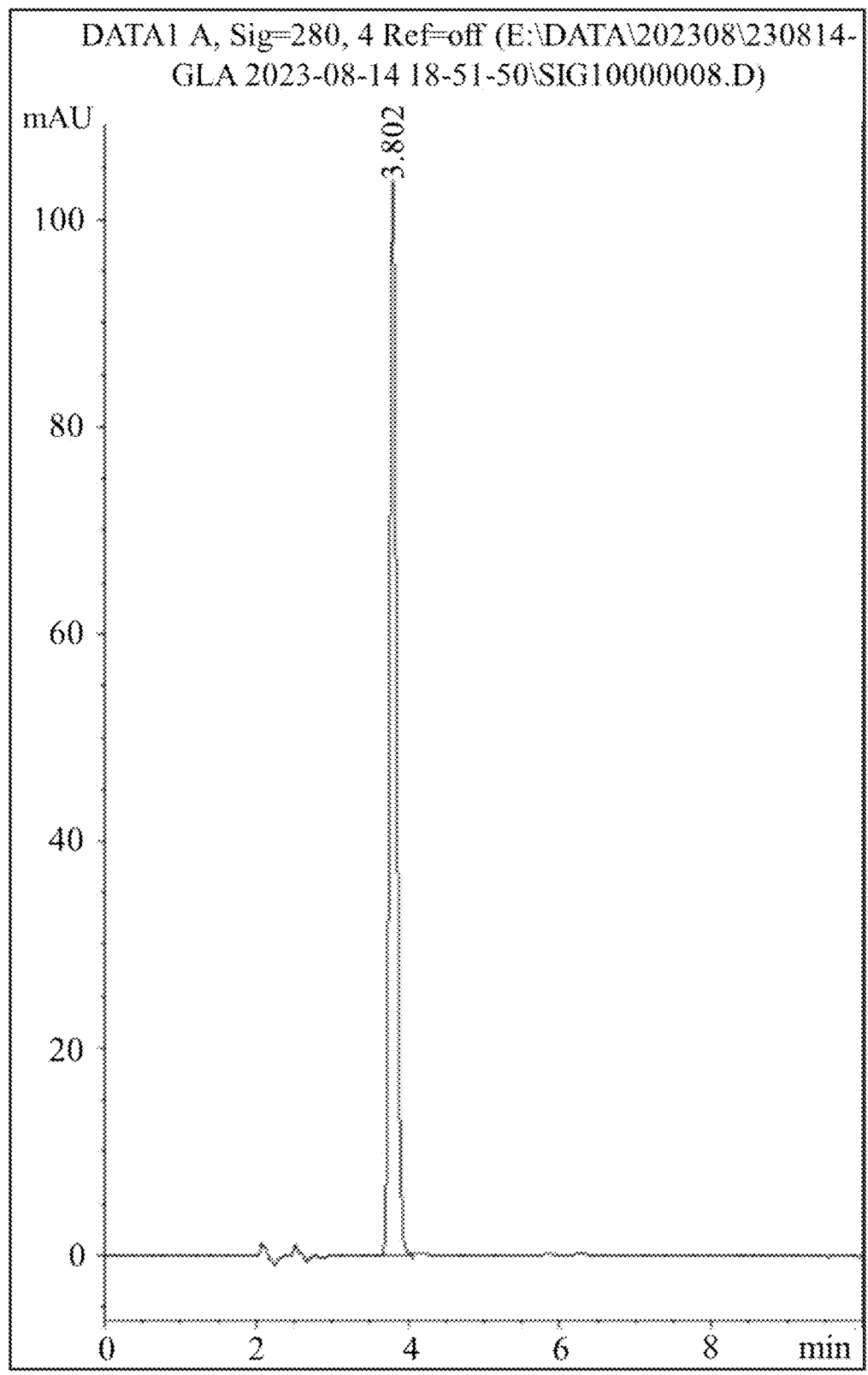

METHOD MELT CRYSTALLIZATION FOR PREPARING HIGH-PURITY GLABRIDIN

CROSS REFERENCE TO RELATED APPLICATIONS

This application claims the priority benefit of Chinese Patent Application Serial Number 202311064877.2, filed on Aug. 22, 2023, the full disclosure of which is incorporated herein by reference.

TECHNICAL FIELD

The present invention pertains to the field of chemical purification, specifically relates to a melt crystallization method for preparing high-purity glabridin.

BACKGROUND OF THE INVENTION

Radix Glycyrrhizae is mainly distributed in the western regions of China and is a traditional Chinese medicinal herb with a long history of use. In Western countries, Radix Glycyrrhizae is primarily used as a flavoring agent, tobacco additive, and expectorant. The "Pharmacopoeia of the People's Republic of China" identifies three types of licorice plants for medicinal: *Glycyrrhiza uralensis*, *Glycyrrhiza inflata*, and *Glycyrrhiza glabra*, including the dried roots and rhizomes. Wherein *Glycyrrhiza glabra*, which has a salt tolerance limit of <10% and poor drought resistance, is sporadically distributed and has the lowest yield, only be found in Xinjiang Uygur Autonomous region.

Glabridin, a unique isoflavone component found in *Glycyrrhiza glabra*, is known for its multiple whitening effect and good safety profile. It is extensively used in the cosmetics industry. The chemical structure of glabridin is represented by the following formula:

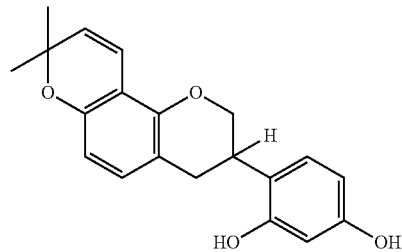 [SMILES: CC1(C)C=Cc2c(ccc3c2OCC(c2ccc(O)cc2O)C3)O1]

Glabridin currently can be extracted from the roots of *Glycyrrhiza glabra*. Since the content of glabridin in *Glycyrrhiza glabra* is only about two per thousand, the process for extracting high-purity glabridin is very complicated and the cost is high. The fixed specification of glabridin in the market mainly comprises 40% and 90% of glabridin, the purity of 40% can be easily achieved after crude extraction, but the color of the glabridin product with the specification of 40% is yellow, and the glabridin product is added into cosmetics to influence the color of the cosmetics. The demand of colorless high-purity glabridin is inevitably raised for high-level requirement customer groups. The color of the glabridin product with the specification of 90% is white, but multiple recrystallizations are needed to achieve the purity of more than 90%, the more recrystallization times, the higher the purity, the purity can reach more than 98%, and the production cost is higher.

High-purity glabridin is in short supply, the prices of glabridin with a 95% purity (determined by High Performance Liquid Chromatography, HPLC) fetches as high as 400,000 yuan per kilogram. The purity of the product obtained by the current domestic production process is difficult to reach the level, and toxic organic solvents such as chloroform, methanol and the like are mostly adopted in the production. The melt crystallization technology has the advantages of no solvent, low energy consumption, small equipment volume, capability of obtaining high-purity products and the like, and is widely applied to the field of separation and purification of organic compounds. The principle is that the separated component is crystallized and separated from the molten liquid by controlling the input and the removal of heat by utilizing the difference of freezing points among the components of the separated substance, and the separation and the purification of the target component are realized through operations such as washing, sweating and the like. According to statistics, hundreds of thousands of tons organic compounds are separated and purified by a melt crystallization method at present, for example, the production scale of the p-dichlorobenzene with the mass fraction as high as 99.99% reaches 17000 t/a; the production scale of 99.95% of p-xylene reaches 70000 t/a; the production scale of bisphenol A reaches 15000 t/a.

Therefore, a method for purifying glabridin by utilizing melt crystallization techniques has very important social significance and economic value, and is simple in establishment process, low in cost and relatively safe.

SUMMARY OF THE INVENTION

Regarding the purification process of glyphosate mentioned above, there are technical problems such as low prepared product purity, large solvent consumption, and high energy consumption. The present invention provides a melt crystallization method for purifying glabridin. Melt crystallization techniques are utilized in the method to purify glabridin, and according to process requirements, secondary or higher crystallization can be used. The product obtained from the technical solutions of the present invention has a purity of over 99.9%. This method has the characteristics of simple operation, no need of solvent, high product purity, environmental protection, and low energy consumption. The technology is suitable for high demand of the market on high-purity glabridin, and has strong market competitive advantages.

In order to solve the technical problem, the following technical solutions are provided:

A melt crystallization method for preparing high-purity glabridin, including the following steps:

Step 1) purification: dissolving crude glabridin with a mass percentage of ≥40% in a solvent, then adsorbing with macroporous adsorption resin AB-8, eluting with ethanol, and recrystallizing to obtain glabridin coarse material;

Step 2) heating and melting: adding the obtained glabridin coarse material into a melting crystallizer, and melting the material to be liquid at a melting temperature;

Step 3) cooling and crystallizing: cooling the glabridin coarse material in the step 2), controlling the cooling rate at 10° C./h to 30° C./h, and the final cooling temperature is at 155° C. to 160° C.; keeping at a constant temperature for 0.5 to 4 hours to crystallize glabridin, and collecting the uncrystallized residual liquid for reuse in the next batch;

Step 4) sweating: sweating the crystals at the heating rate of 1 to 15° C./h after discharging the uncrystallized mother liquor, heating up to 160° C. to 168° C., keeping at a constant temperature for 0.5 to 2 hours, discharging the sweating liquid, and reusing it in the next batch;

Step 5) melting: heating to raise the temperature to above 175° C. after discharging the sweating liquid, completely melting the materials, and collecting the molten liquid as the feeding material of the next-stage crystallization;

Step 6) repeating steps 3) to 5) for multi-stage crystallization, collecting molten liquid, cooling, and crystallizing to obtain the glabridin with a purity greater than 99.9%, resulting in ultra-high-purity glabridin.

In some embodiments, the solvent in step 1) is selected from one of butanediol and propylene glycol.

In some embodiments, the recrystallization solvent in step 1) is selected from one of ethanol, methanol, isopropanol, propanol, butanediol and propylene glycol. In some embodiments, the recrystallization solvent in step 1) is propanol.

In some embodiments, the cooling rate in step 3) is 15° C./h to 20° C./h.

In some embodiments, the final cooling temperature in step 3) is 156° C. to 159° C.

In some embodiments, the constant temperature time in step 3) is 1 to 3 hours.

In some embodiments, the heating rate in step 4) is 5° C./h to 10° C./h.

In some embodiments, the final sweating temperature in step 4) is 162° C. to 166° C.

In some embodiments, the constant temperature in step 4) is 1~1.5 h.

In some embodiments, the melt crystallization method for preparing high-purity glabridin, characterized in that the method includes the following steps: adding crude glabridin with a content greater than 40% into a melt crystallizer, and heating up and melting the material to be liquid; cooling the material at a cooling rate at 10° C./h to 30° C./h with the final cooling temperature at 155° C. to 160° C.; keeping at a constant temperature for 0.5 to 4 hours; discharging the mother liquor, heating the material at a rate of 1° C./h to 15° C./h up to 160° C. to 168° C., keeping at a constant temperature for 0.5 h to 2 h, for sweating; discharging the sweating liquid; heating to above 175° C., melting and discharging the material, collecting the molten liquid for secondary crystallization, and finally collecting the molten liquid, cooling, and crystallizing to obtain ultra-high-purity glabridin.

In some embodiments, the crude glabridin in step 1) is obtained commercially or separated by extraction, silica gel column chromatography, recrystallization, preparative liquid phase, macroporous adsorbent resin separation method.

According to the process requirements, secondary or higher-level crystallization can be used. If secondary crystallization is adopted, the primary mother liquor enters a secondary crystallizer, primary sweating liquid flows back to the primary crystallizer as a raw material, and a primary product is produced by the primary crystallizer; the secondary sweating liquid and the primary mother liquid are mixed and pumped into the secondary crystallizer again, the secondary product, the raw material and the primary sweating liquid are mixed and pumped into the primary crystallizer again.

The glabridin is separated and purified according to the method, the glabridin is suitable for crude glabridin products with the percentage content is ≥40%, preferably ≥80%), raw materials of the process enter a separation process, and except secondary mother liquor obtained by recrystallizing the mother liquor, materials obtained in other steps can be used as primary raw materials or secondary raw materials.

The invention has the advantages and beneficial effects that:

1. The present invention provides a melt crystallization method for purification, and ultra-high purity products with purity more than 99.9% can be obtained. This method has the characteristics of simple operation, no need for a large amount of solvent, high product purity, environmental protection, and low energy consumption. It is a green separation and purification process. The technology is suitable for high demand of the market on high-purity glabridin, and has strong market competitive advantages.

2. In this invention, all materials except for the secondary mother liquor can be recycled, resulting in high raw material utilization.

It should be understood that in the description of the present invention, terms such as "first," "second" are used only for descriptive purposes and should not be construed as indicating or implying relative importance or implicitly indicating the quantity of the indicated technical features. Thus, features defined with "first," "second" can explicitly or implicitly include one or more of these features. In the description of the present invention, "more" means two or more unless specifically defined otherwise.

In the description of the invention, the terms "one embodiment," "some embodiments," "an example," "a specific example," or "some examples" or the like means refer to specific features, structures, materials, or characteristics included in at least one embodiment or example of the invention. In this document, schematic representations of such terms do not necessarily refer to the same embodiment or example. Furthermore, the specific features, structures, materials, or characteristics described may be combined in any suitable manner in one or more embodiments or examples. Additionally, in the absence of any conflict, those skilled in the art can combine and integrate different embodiments or examples and features of different embodiments or examples described in this document.

BRIEF DESCRIPTION OF DRAWINGS

FIG. 1 presents the chromatogram of high-purity glabridin prepared in Example 1.

DESCRIPTION

In order to make the technical solutions of the present invention better understood by those skilled in the art, some non-limiting examples are further disclosed below to further explain the present invention in detail.

The reagents used in this invention can be purchased from the market or prepared using the methods described in this invention.

In this invention, "min" represents minute or minutes; "h" represents hour or hours; "g" represents gram or grams; "mL" represents milliliters or milliliters; "mg" represents milligram or milligrams.

In this invention, the detection of glabridin content is carried out using high-performance liquid chromatography (HPLC) as per "QBT4951-2016 Cosmetic Raw Material *Glycyrrhiza Glabra* Root Extract."

In this invention, "room temperature" refers to 10° C.-40° C.

In this invention, "single pass yield" refers to the mass of high-purity product obtained in the first-stage melt crystallization divided by the mass of crude product input, multiplied by 100%.

Example 1

In a 500 mL melt crystallizer, 50 g of 40.5% glabridin crude product was added and dissolved in propylene glycol, then adsorbed with macroporous resin AB-8, followed by eluted with 90% ethanol. The eluent was collected and concentrated in vacuum to remove some solvent, then recrystallized with 50 mL of propanol at room temperature. The crystals were filtered, collected, and dried to obtain glabridin coarse material. This glabridin coarse material was heated to 160° C. until it was completely melted into a liquid state. It was then cooled at a rate of 20° C./h to a final temperature of 158° C., and maintained at this temperature for 2 hours. The mother liquor was discharged, and the material was heated at a rate of 10° C./h to 165° C., and maintained for 1 hour for sweating. The sweating liquid was discharged. The material was then heated to above 175° C., melted and discharged the material, and the molten liquid was collected for secondary crystallization. Finally, the molten liquid was collected, cooled, and crystallized to obtain ultra-high-purity glabridin with a product purity of 99.94% and a single pass yield of 74.5%.

Example 2

In a 500 mL melt crystallizer, 20 g of 40.5% glabridin crude product was added and dissolved in propylene glycol, then adsorbed with macroporous resin AB-8, followed by eluted with 95% ethanol. The eluent was collected and concentrated in vacuum to remove some solvent, then recrystallized with 20 mL of propanol at room temperature. The crystals were filtered, collected, and dried to obtain glabridin coarse material. This glabridin coarse material was heated to 160° C. until it was completely melted into a liquid state. It was then cooled at a rate of 10° C./h to a final temperature of 158° C., and maintained at this temperature for 2 hours. The mother liquor was discharged, and the material was heated at a rate of 5° C./h to 165° C., and maintained for 1 hour for sweating. The sweating liquid was discharged. The material was then heated to above 175° C., melted and discharged the material, and the molten liquid was collected for secondary crystallization. Finally, the molten liquid was collected, cooled, and crystallized to obtain ultra-high-purity glabridin with a product purity of 99.96% and a single pass yield of 52.0%.

Example 3

In a 500 mL melt crystallizer, 10 g of 40.5% glabridin crude product was added and dissolved in butanediol, then adsorbed with macroporous resin AB-8, followed by eluted with 95% ethanol. The eluent was collected and concentrated in vacuum to remove some solvent, then recrystallized with 15 mL of propanol at room temperature. The crystals were filtered, collected, and dried to obtain glabridin coarse material. This glabridin coarse material was heated to 165° C. until it was completely melted into a liquid state. It was then cooled at a rate of 30° C./h to a final temperature of 158° C., and maintained at this temperature for 2 hours. The mother liquor was discharged, and the material was heated at a rate of 2° C./h to 165° C., and maintained for 1 hour for sweating. The sweating liquid was discharged. The material was then heated to above 175° C., melted and discharged the material, and the molten liquid was collected for secondary crystallization. Finally, the molten liquid was collected, cooled, and crystallized to obtain ultra-high-purity glabridin with a product purity of 99.96% and a single pass yield of 52.0%.

Reaction Conditions Study

Example 4

According to the procedure described in example 1, 50 g of 40.5% glabridin crude product was added and dissolved in propylene glycol, then adsorbed with macroporous resin AB-8, followed by eluted with 95% ethanol. The eluent was collected and concentrated in vacuum to remove some solvent, then recrystallized with 50 mL of propanol at room temperature. The crystals were filtered, collected, and dried to obtain glabridin coarse material. The glabridin coarse material was subjected to melt crystallization, the effects of process conditions on the product purity and the single pass yield were investigated, and the results are represented in the following table.

| Initial crystallization temperature (° C.) | Final crystallization temperature (° C.) | Crystallization time (min) | Sweating initial temperature (° C.) | Sweating final temperature (° C.) | Sweating time (min) | Purity % | Single pass yield % |
|---|---|---|---|---|---|---|---|
| 165 | 159 | 30 | 157 | 158 | 60 | 99.94 | 77.5 |
| 165 | 159 | 20 | 157 | 158 | 50 | 99.96 | 76.2 |
| 175 | 160 | 20 | 157 | 159 | 60 | 99.99 | 65.3 |
| 175 | 160 | 10 | 157 | 159 | 50 | 99.95 | 55.9 |
| 175 | 160 | 5 | 157 | 159 | 60 | 99.95 | 47.1 |

Comparative Example 1

In a 500 mL melt crystallizer, 50 g of 40.5% glabridin crude product was added and dissolved in propylene glycol, then adsorbed with macroporous resin AB-8, followed by eluted with 95% ethanol. The eluent was collected and concentrated in vacuum to remove some solvent, then recrystallized with 50 mL of propanol at room temperature. The crystals were filtered, collected, and dried to obtain glabridin coarse material. This glabridin coarse material was heated to 160° C. until it was completely melted into a liquid state. It was then cooled at a rate of 20° C./h to a final temperature of 158° C., and maintained at this temperature for 2 hours. The mother liquor was discharged, and the material was heated at a rate of 10° C./h to 165° C., and maintained for 1 hour for sweating. The sweating liquid was discharged. The material was then heated to above 175° C., melted and discharged the material, cooled and crystallized to obtain ultra-high-purity glabridin with a product purity of 99.1% and a single pass yield of 71.2%.

Comparative Example 2

In a 500 mL melt crystallizer, 50 g of 40.5% glabridin crude product was added and dissolved in propylene glycol, then adsorbed with macroporous resin AB-8, followed by eluted with 95% ethanol. The eluent was collected and concentrated in vacuum to remove some solvent, then recrystallized with 50 mL of propanol at room temperature. The crystals were filtered, collected, and dried to obtain glabridin coarse material. This glabridin coarse material was heated to 175° C. until it was completely melted into a liquid state. It was then cooled at a rate of 20° C./h to a final temperature of 155° C., and maintained at this temperature for 2 hours. The mother liquor was discharged, and the material was heated at a rate of 10° C./h to 170° C., and maintained for 1 hour for sweating. The sweating liquid was discharged. The material was then heated to above 175° C., melted and discharged the material, cooled and crystallized to obtain ultra-high-purity glabridin with a product purity of 95.3% and a single pass yield of 61.2%.

Comparative Example 3

In a 500 mL melt crystallizer, 50 g of 40.5% glabridin crude product was added and dissolved in propylene glycol, then adsorbed with macroporous resin AB-8, followed by eluted with 95% ethanol. The eluent was collected and concentrated in vacuum to remove some solvent, then recrystallized with 50 mL of propanol at room temperature. The crystals were filtered, collected, and dried to obtain glabridin coarse material. This glabridin coarse material was heated to 160° C. until it was completely melted into a liquid state. It was then cooled at a rate of 8° C./h to a final temperature of 158° C., and maintained at this temperature for 2 hours. The mother liquor was discharged, and the material was heated at a rate of 20° C./h to 165° C., and maintained for 1 hour for sweating. The sweating liquid was discharged. The material was then heated to above 175° C., melted and discharged the material, cooled and crystallized to obtain ultra-high-purity glabridin with a product purity of 89.4% and a single pass yield of 51.1%.

The methods of this invention have been described through preferable examples, and it is apparent to those skilled in the art that variations or appropriate modifications and combinations may be made to implement and use the techniques of the present invention within the intended scope, spirit and scope of the invention. Those skilled in the art can modify the process parameters appropriately in view of the disclosure herein. It is specifically noted that all such substitutions and modifications will be apparent to those skilled in the art and are intended to be included within the present invention.

The invention claimed is:

1. A melt crystallization method for preparing high-purity glabridin, characterized in that the method includes the following steps:
   Step 1) purification: dissolving crude glabridin with a mass percentage of ≥40% in a solvent, then adsorbing with macroporous adsorption resin AB-8, eluting with ethanol, and recrystallizing to obtain glabridin coarse material;
   Step 2) heating and melting: adding the obtained glabridin coarse material into a melting crystallizer, and completely melting the material to be liquid at a melting temperature;
   Step 3) cooling and crystallizing: cooling the glabridin liquid material of step 2) by controlling the cooling rate at 10° C./h to 30° C./h to a final cooling temperature of 155° C. to 160° C.: keeping said temperature constant for 0.5 to 4 hours to obtain crystals of glabridin; and collecting the uncrystallized residual liquid;
   Step 4) sweating: sweating the crystals by heating the crystals up to 160° C. to 168° C. at a heating rate of 1° C./h to 15° C./h; and keeping said temperature constant for 0.5 to 2 hours, wherein the sweating liquid is discharged,
   Step 5) melting: heating to raise the temperature of the crystals to above 175° C. after discharging the sweating liquid, completely melting the crystals to be molten liquid, and collecting the molten liquid;
   Step 6) repeating steps 3) to 5) on the collected molten liquid of step 5) for multi-stage crystallization, after repeating one or more times, collecting the molten liquid, cooling, and crystallizing the collected molten liquid to obtain the glabridin, resulting in ultra-high-purity glabridin.

2. The method according to claim 1, characterized in that the crude glabridin in step 1 is obtained commercially or separated by extraction, silica gel column chromatography, recrystallization, preparative liquid phase chromatography or macroporous adsorbent resin separation method.

3. The method according to claim 1, characterized in that the cooling rate in step 3) is 15° C./h to 20° C./h.

4. The method according to claim 1, characterized in that the final cooling temperature in step 3) is 156° C. to 159° C.

5. The method according to claim 1, characterized in that the constant temperature time in step 3) is 1 to 3 hours.

6. The method according to claim 1, characterized in that the heating rate in step 4) is 5° C./h to 10° C./h.

7. The method according to claim 1, characterized in that the final heating sweating-temperature in step 4) is 162° C. to 166° C.

8. The method according to claim 1, characterized in that the constant temperature time in step 4) is 1 to 1.5 hours.

9. A melt crystallization method for preparing high-purity glabridin, characterized in that the method includes the following steps: dissolving crude glabridin with a mass percentage of ≥40% in a solvent, then adsorbing with macroporous adsorption resin AB-8, eluting with ethanol, and recrystallizing to obtain glabridin coarse material; adding the obtained glabridin coarse material into a melting crystallizer, and heating up and melting the material to be liquid; cooling the liquid at a cooling rate of 10° C./h to 30° C./h with the final cooling temperature of 155° C. to 160° C.; keeping said temperature constant for 0.5 to 4 hours to obtain crystals of glabridin; discharging the mother liquor; heating the crystals at a rate of 1° C./h to 15° C./h up to 160° C. to 168° C., keeping said temperature constant for 0.5 h to 2 h, for sweating; discharging the sweating liquid; heating the crystals to above 175° C.; melting the crystals to be molten liquid; and finally collecting the molten liquid, cooling, and crystallizing it to obtain ultra-high-purity glabridin.

* * * * *